United States Patent
Swain et al.

(10) Patent No.: US 6,630,610 B2
(45) Date of Patent: Oct. 7, 2003

(54) METHOD OF PRODUCING FLUORINATED ORGANIC COMPOUNDS

(75) Inventors: Charles F. Swain, Erie County, NY (US); Stephen A. Cottrell, East Baton Rouge, LA (US); Clifford Scott Riegel, East Baton Rouge, LA (US); Curtis A. Brescher, East Baton Rouge, LA (US)

(73) Assignee: AlliedSignal Inc., Morristown, NJ (US)

( * ) Notice: Subject to any disclaimer, the term of this patent is extended or adjusted under 35 U.S.C. 154(b) by 0 days.

(21) Appl. No.: 09/800,126

(22) Filed: Mar. 6, 2001

(65) Prior Publication Data

US 2001/0034465 A1 Oct. 25, 2001

Related U.S. Application Data

(63) Continuation of application No. 09/008,132, filed on Jan. 16, 1998, now abandoned.

(51) Int. Cl.$^7$ ............................................. C07C 17/00
(52) U.S. Cl. .................... 570/167; 570/161; 570/164
(58) Field of Search ................. 570/167, 164, 570/161

(56) References Cited

U.S. PATENT DOCUMENTS

| 4,091,043 A | 5/1978 | Ohsaka et al. ............ 260/653.7 |
| 5,545,773 A | 8/1996 | Berthe ........................ 570/167 |
| 5,569,793 A | 10/1996 | Bergougnan et al. ....... 570/167 |

FOREIGN PATENT DOCUMENTS

| JP | WO 95/35271 | 12/1995 |
| WO | WO 96/05156 | * 2/1996 |

* cited by examiner

Primary Examiner—J. Parsa
(74) Attorney, Agent, or Firm—Colleen D. Szuch

(57) ABSTRACT

A process for producing a fluorinated organic compound comprising: (a) reacting an organic starting material with a fluorination agent in the presence of a liquid fluorination catalyst under conditions which are effective to vaporize one or more chlorinated organic by-products and to produce a gaseous product stream containing said fluorinated organic compound and said one or more chlorinated organic by-products; and (b) recovering said fluorinated organic compound from said product stream, and a system for performing the aforementioned process and recovering the chlorinated by-product.

20 Claims, 1 Drawing Sheet

METHOD OF PRODUCING FLUORINATED ORGANIC COMPOUNDS

REFERENCE TO RELATED APPLICATION

This is a continuation application of U.S. application Ser. No. 09/008,132, filed Jan. 16, 1998 now is abandoned.

FIELD OF INVENTION

The present invention relates generally to the preparation of fluorinated organic compounds. More specifically, the invention relates to the preparation of fluorinated organic compounds by a liquid-phase, catalytic fluorination process.

BACKGROUND OF THE INVENTION

The production of fluorinated organic compounds, such as hydrofluorocarbons (HFCs) and hydrochlorofluorocarbons (HCFCs), is well known in the art. Among the more popular fluorination methods is liquid-phase, catalytic fluorination which is of particular interest herein. In this type of fluorination, a liquid starting material is reacted with a fluorination agent in a reactor in the presence of a liquid catalyst and under conditions sufficient to form a fluorinated organic compound. The fluorinated organic compound readily vaporizes under the reaction conditions and leaves the reactor as a vapor in a product stream. The product stream then is distilled to recover the fluorinated organic compound.

Although widely used, conventional liquid-phase fluorination suffers from several shortcomings. One of the more significant shortcomings is the formation of high-boiling by-products. As used herein, "by-product" refers to any compound that is produced in the fluorination process and that is neither the desired HFC/HCFC, nor a fluorinated intermediate. The most common by-products are chlorinated by-products. Chlorinated by-products are formed at particularly high levels when chlorine is added to the reaction to regenerate the catalyst. For example, in the production of 1,1,1-trifluoroethane (HFC-143a), the use of chlorine increases substantially the formation of the by-product 1,2-dichloro-1,1-difluoroethane (HCFC-132b). Chlorinated by-products can be formed also in side reactions with the fluorination catalyst.

Chlorinated by-products tend to have higher boiling points than those of the fluorinated product; consequently, they tend not to vaporize during fluorination. Over time, the chlorinated by-products accumulate in the reactor necessitating periodic shut-downs to boil off or drain them from the reactor. Shutting down the reactor disrupts the continuous fluorination process and thereby reduces production efficiency. Additionally, once accumulation of by-products begins, the space available for fluorination decreases, thereby further reducing production efficiency. Therefore, a need exists for a more efficient approach to preparing HFCs and HCFCs, including an approach that avoids the accumulation of high-boiling by-products in the reactor. The present invention fulfills this need among others.

DESCRIPTION OF THE INVENTION AND PREFERRED EMBODIMENTS

Figure 1:
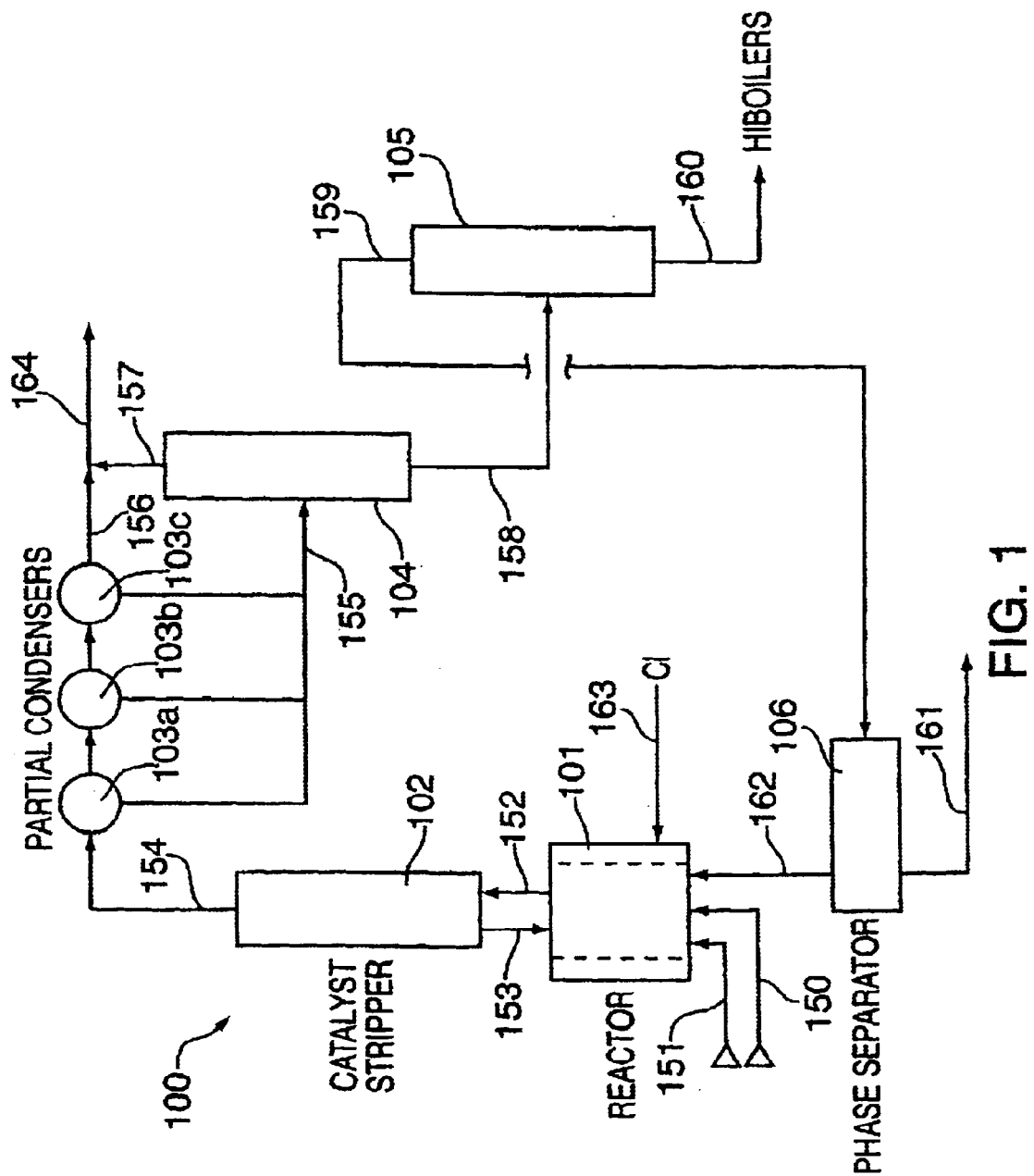
FIG. 1 shows a schematic system diagram of a preferred embodiment of the present invention.

The present invention provides for the preparation of fluorinated organic compounds while avoiding the accumulation of high-boiling by-products in the reactor by operating at conditions sufficient to vaporize the by-products. More specifically, the fluorination reaction is operated at elevated temperatures and/or at reduced pressures such that one or more high-boiling by-products are volatilized and exit the reactor in the product stream. These high-boiling by-products then can be removed from the fluorination system using conventional techniques. Therefore, by vaporizing the high-boiling by-products, the present invention allows for the recovery of the by-product from the product stream and thereby eliminates the need to shut-down and drain the reactor.

Conventional fluorination practice generally teaches away from operating under the conditions of the present invention since the reactants also tend to be volatilized. Volatilizing the reactants reduces the time they reside in the reactor and are available to react. One would therefore expect the fluorination of the present invention to have lower conversion levels than those of conventional fluorination. Surprisingly, this is not the case. The use of an increased catalyst concentration and a higher reaction temperature in accordance with the present invention results in an increased reaction rate which tends to convert reactants to product before they are vaporized.

One aspect of the invention is the provision of a process for preparing a fluorinated organic compound in which the accumulation of by-products in the reactor is reduced or eliminated. In one embodiment, the process comprises: (a) reacting an organic starting material with a fluorination agent in the presence of a liquid-phase fluorination catalyst under conditions sufficient to vaporize one or more chlorinated organic by-products, and to produce a product stream containing said fluorinated organic and said one or more chlorinated organic by-products; and (b) recovering said fluorinated organic compound from said product stream. Optionally, the chlorinated by-product is also recovered from the product stream. In another embodiment, the process comprises: (a) reacting an organic starting material with a fluorination agent in the presence of a liquid-phase fluorination catalyst under conditions sufficient to vaporize a substantial portion of all of the by-products, and to produce a product stream containing said fluorinated organic and said by-products; and (b) recovering said fluorinated organic compound from said product stream.

The process of the present invention can be practiced in a continuous manner in which the fluorination reaction is conducted under conditions to continuously vaporize the high-boiling by-products. Alternatively, the fluorination process can be conducted at traditional pressures and temperatures to increase reactant residence time and utilization of the reactants and then, periodically, the process of the present invention can be used to vaporize the by-products thereby avoiding accumulation in the reactor.

Another aspect of the invention is the provision of a system for preparing a fluorinated organic compound without accumulating by-products in the reactor and for recovering chlorinated by-products without draining the reactor. In a preferred embodiment, the system comprises: (a) means for reacting an organic starting material with a fluorination agent in the presence of a liquid-phase fluorination catalyst under conditions sufficient, at least periodically, to vaporize substantially one or more chlorinated organic by-products, and to produce a product stream containing said fluorinated organic and said one or more chlorinated organic by-products; (b) means for recovering said fluorinated organic compound from said product stream; and (c) means for recovering said one or more chlorinated by-products from said product stream.

The present invention can be used in the production of a wide variety of HFCs and HCFCs. It is particularly effective in the preparation and co-vaporization of the following fluorinated compounds and chlorinated by-products:

| Fluorinated Compound | Chlorinated By-product |
| --- | --- |
| 1,1,1-trifluoroethane (HFC-143a) | 1,2-dichloro-1,1-difluoroethane (132b) |
| 2-chloro-1,1,1-trifluoroethane (HFC-133a) | 2,2-dichloro-1,1,1-trifluoroethane (123) |
| 1,1,1,3,3,3-hexafluoropropane (HFC-236fa) | 2-chloro-1,1,1,3,3,3-hexafluoropropane (HCFC-226) |
| 1,1,3,3,3-pentafluoropropane (HFC-245fa) | 1-chloro-1,1,3,3,3-pentafluoropropane (HCFC-235fa) |

In the most preferred embodiment, the process is used to prepare HFC-143a.

In preparing the fluorinated compound, the reactants, which include an organic starting material and a fluorination agent, are contacted in a reactor in the presence of a liquid-phase fluorination catalyst.

The organic starting material may be any compound that contains a carbon-bonded chlorine or other atom replaceable by fluorine and/or that contains a carbon-carbon unsaturated bond that is saturatable with fluorine. Suitable organic compounds include, for example, hydrochlorofluorocarbons (compounds containing carbon, chlorine, fluorine and hydrogen), hydrochlorocarbons (compounds containing carbon, chlorine and hydrogen), chlorofluorocarbons (compounds containing carbon, chlorine and fluorine), and chlorocarbons (compounds containing carbon and chlorine) or mixtures of two or more thereof. Preferably, the organic starting material includes, without limitation, a chlorinated hydrocarbon compound containing from 1 to 6 carbon atoms and 1 to 12 chlorine atoms. More preferred organic starting materials include 1,1,1-trichloroethane, 1,1,1,2-tetrachloroethane, 1,1,1,3,3,3-hexachloropropane, and 1,1,3,3,3-pentachloropropane. In the most preferred embodiment, the organic starting material is 1,1,1-trichloroethane.

A suitable fluorination agent includes any material that provides a fluorine atom for fluorination of the organic starting material. A mixture of two or more fluorination agents may be used. Preferred fluorination agents include hydrogen fluoride, elemental fluorine, and boron trifluoride. A more preferred fluorination agent is substantially anhydrous hydrogen fluoride (HF). The presence of water in the reaction tends to deactivate the fluorination catalyst. As used herein, the term "substantially anhydrous" refers to a moisture content of less than about 0.05% by weight and preferably less than about 0.02% by weight. It should be understood, however, that the presence of water in the catalyst can be compensated for by increasing the amount of catalyst used.

The fluorination agent should be supplied to the reaction in an amount to provide at least about a stoichiometric amount of fluorine. For example, based on reaction stoichiometry, the mole ratio of HF to 1,1,1 trichloroethane to form 1,1,1-trifluoroethane should be from about 2.5:1 to about 4:1, preferably from about 3:1 to about 3.6:1, and more preferably from about 3:1 to about 3.1:1.

The reactants can be fed individually or as a mixture to the reactor. Once the reaction is under way, the reactants may be added continuously under pressure to supply the additional amounts of reactants needed to continue the process.

Any suitable fluorination catalyst can be used. Examples of the fluorination catalyst include, but are not limited to, halides, mixed halides, oxides or oxyhalides of Group III, IV, IVb, V, Vb, VIa, VIb or VIII elements, such as, for example, $SbCl_5$, $TiCl_4$, $SnCl_4$, and $BF_3$. Preferably, the fluorination catalyst is an antimony containing compound, more preferably, a pentavalent antimony compound. The pentavalent antimony compounds can be a halide, for example, $SbCl_5$ and $SbF_5$; a mixed halide of the formula $SbCl_xF_y$ where x ranges from 1 to 5 and y ranges from 0 to 4 provided that x+y=5, for example, $SbCl_3F_2$ and $SbCl_2F_3$; and a mixture of halide catalysts, for example, a mixture of $SbF_5$ and $SbCl_5$. The most preferred fluorination catalyst is antimony pentachloride.

Although the amount of fluorination catalyst used may vary widely, it is generally preferred to use a greater amount than that used traditionally. That is, since fluorination performed under conditions according to the present invention results in the increased vaporization of the reactants, the reactants have less of an opportunity to react. Therefore, it is desirable to increase the concentration of catalyst to increase the reaction rate. The weight percent of catalyst based on the weight of the reaction mixture is preferably from about from about 5 to about 80%, and more preferably from about 15 to about 50%. As used herein, the term "reaction mixture" refers to the mixture of materials present in the reactor, including the reactants, catalyst, fluorinated organic compound product, and by-products.

It should be noted that the catalyst concentration in the reaction mixture affects the concentration of fluorinated intermediates in the product stream. More specifically, lower concentrations result in lower conversion levels. Lower conversion levels mean that less of the fluorinated intermediates are being converted to product. Consequently, the concentration of the fluorinated intermediates increases in the product stream. If the fluorinated intermediate is a desired co-product, such as, for example, HCFC-142b, then it may be desirable to use catalyst concentrations less than those as described above.

It may be advantageous to regenerate the catalyst periodically or continuously. Procedures for doing this are known in the art and typically involve the addition of an oxidizing agent to the reaction. One of ordinary skill in the art can determine readily the amount of agent to be added to optimize the use of the catalyst. In the preferred embodiment, chlorine is metered into the reaction mass in order to keep the fluorination catalyst active. For example, in the production of HFC-143a, the weight ratio of chlorine feed to the organic starting material feed is preferably about 0.01 to about 0.05, and more preferably, about 0.01 to about 0.02.

The reaction is conducted under conditions sufficient to meet two objectives: to effect fluorination and to vaporize one or more high-boiling by-products. These two objectives may be met under the same operating conditions or they can be met individually by periodically alternating the reaction conditions.

The operating conditions should be such that a significant portion of the by-products are vaporized. In one preferred embodiment, no less than 50% by weight of the by-products are vaporized, and more preferably no less than about 75%. Even more preferably, essentially all of the by-products are vaporized. In another preferred embodiment, the operating conditions are such that by-product accumulation is no greater than about 2% by weight of organic starting material feed, and even more preferably no greater than about 1%. In a still more preferred embodiment, there is essentially no by-product accumulation. In another preferred embodiment, the pressure is just low enough to vaporize one or more chlorinated by-products for a given temperature, more preferably, the pressure is just low enough to vaporize essentially all of the chlorinated by-products for a given temperature. One skilled in the art can determine readily the pressure at which a compound will vaporize for a given temperature.

It has been found that reaction temperatures of about 60 to about 120° C., preferably, about 70 to about 100° C., and reaction pressures of about 50 to about 250 psig, preferably, about 50 psig to about 100 psi, are adequate to fluorinate chlorinated starting materials, such as HCFC-140a (to form HFC-143a), and to vaporize the high-boiling by-products, such as HCFC-132b.

Although the operating conditions described above also tend to reduce the time the reactants reside in the reactor, it has been found that with increased temperature and catalyst concentrations acceptable conversation levels are achievable. For example, the conversion of 1,1,1-trichloroethane to 1,1,1-trifluoroethane typically ranges from bout 95% to about 99.9%. The conversion of hydrogen fluoride to 1,1, 1-trifluoroethane typically ranges from about 93% to about 98%. The high conversion levels of the present invention result in commercially-acceptable production rates, preferably, at least about 10 lb/hr/ft$^3$ of reactor volume.

Alternatively, the reactor is operated at a temperature and pressure so as to retain reactants (along with by-product) in the reactor and, periodically, the pressure is reduced to allow by-products to vaporize. When by-product content in the reactor is reduced to acceptable levels, pressure is raised again to increase residence time of the reactants.

Referring to FIG. 1, a preferred embodiment of a reactor system 100 of the present invention is shown. The reactor system 100 comprises a reactor 101, a catalyst stripper 102, partial condensers 103a–c, a first distillation unit 104, a second distillation unit 105, and a phase separator 106. Depending upon the heating requirements, an optional preconditioner system (not shown) may be used to preheat a liquid stream 151 and to vaporize and superheat a vapor stream 150. Streams 151 and 150 are fed into the reactor 101. The reactor 101 facilitates liquid-phase fluorination and may comprise any apparatus conventionally used for preparing fluorinated compounds by liquid-phase fluorination. Such apparatus is well known and may consist of one or more reactor vessels depending upon desired reaction rates and economic constraints. An example of a satisfactory apparatus for this purpose is a single reaction vessel, such as autoclave, to which the reaction materials can be added, in liquid or gaseous form, and heated to the desired reaction temperature. Heating may be effected by heating the reaction materials and/or by equipping the reactor with a heating jacket or internal coil. The process of the present invention does not require mechanical agitation of the reactants, thus simplifying the reaction apparatus and procedures.

The reaction vessel 101 should be capable of sustaining reaction pressures up to about 300 psi or whatever the maximum reaction pressure is expected to be. Because the reaction occurs typically under pressure, the reactor is generally comprised of metal or other structurally rigid material. Suitable materials include, for example, stainless steel, Inconel alloy, Monel alloy, Hastelloy, or other type of a structurally suitable alloy.

Reactor 101 can be lined with a fluoropolymer for general corrosion resistance. As used herein, the terms "fluorinated polymer" and "fluoropolymer" are used interchangeably and broadly refer to any polymer, copolymer or blend of polymers having a fluoride atom in at least one of the monomers from which the polymers are made. Preferred materials include, for example, polytetrafluoroethylene, poly (vinylidene fluoride), ethylene-tetrafluoroethylene polymer, ethylene-hexafluoropropylene polymer, tetrafluoroethylene-hexafluoropropylene polymer, perfluoroalkoxy polymer, any modified version of the above-mentioned polymers, and blends of two or more thereof. Polytetrafluoroethylene or its modified version is particularly preferred.

Liquid-phase fluorination within reactor 101 produces a vaporized product stream 152 which is fed into the catalyst stripper 102. The catalyst stripper removes a substantial portion of the entrained or gaseous catalyst complex from the product stream 152. Preferably, the catalyst complex is returned to the reactor 101, for example, by gravity in the form of steam 153. In the latter embodiment, it may be preferable to have the catalyst stripper 102 mounted atop the reactor 101. The bulk removal of the catalyst in the catalyst stripper reduces the corrosiveness of the product stream which in turn allows for post-reaction apparatus such as reboilers and recycle preconditioners.

Suitable catalyst s include any apparatus that removes a high-boiling point component from a vapor feed by contacting it with a reflux liquid having a low concentration of the high-boiling point component. In applications involving particularly corrosive catalysts, the catalyst stripper is preferably lined, coated, or otherwise protected by a fluoropolymer as defined above.

A scrubbing liquid, preferably a recycle stream (not shown), can be used to scrub catalyst from the product stream 152 to form a low-catalyst content product stream 154. The scrubbing liquid preferably has no catalyst vapor partial pressure or lower pressure than the product stream 152. Suitable scrubbing liquids include, for example, organic starting material, intermediate product, product, fluorination agent, and a low-boiling fraction stream 159 from the second distillation unit 105. A substantial amount of scrubbed catalyst is returned to the reactor by the scrubbing liquid in return stream 153.

The weight ratio of scrubbing liquid to product stream (herein "ratio") is low compared to the first distillation unit. The ratio is relatively low because it is intended to scrub only those high-boiling components which are readily removable. The corrosive catalyst vapors tend to have high-boiling points and condense readily upon contact with the scrubbing liquid. Therefore, high ratios are not necessary. The ratio is preferably no greater than about 0.5/1, more preferably no greater than about 0.3/1, and even more preferably no greater than 0.2/1.

The fluorinated organic compound can be recovered from the low-catalyst content product stream 154 by distilling the stream 154 directly. However, it is preferred to first subject the stream to one or more partial condensers. Since the fluorinated organic compound tends to have a lower boiling point than other constituents of the product stream, such as, for example, unreacted starting material and chlorinated by-products, the partial condensers can be operated at a temperature sufficient to liquify most of the by-product and other high-boiling constituents while a substantial portion of the fluorinated product remains a vapor. The low-catalyst content product stream 154 is fed through partial condensers 103a–c to separate the low-catalyst content product stream 154 into a liquid product stream 155 and a vapor product stream 156. This way only the liquid product stream 155 needs to be distilled.

The stream 155 is fed to the first distillation unit 104. Using conventional distillation techniques, the first distillation unit generates a low-boiling fraction stream 157 and a high-boiling fraction stream 158. Suitable first distillation units are well known in the art and include any conventional distillation apparatus, such as, packed column units and tray column units. In a preferred embodiment, the catalyst stripper and the first distillation unit are constructed as a single column. In applications involving particularly corrosive catalysts, the first distillation unit and its peripheral equipment are preferably lined, coated, or otherwise protected by a fluoropolymer as described above.

The low-boiling fraction stream 157 enters a condenser (not shown) where a portion condenses and refluxes to the first distillation unit, while the remaining portion joins stream 156 from the partial condensers to form the refined product stream 164. The fluorinated product is then recovered from stream 164 using conventional purification techniques, typically distillation. The details of this recovery are not described herein since they are well known in the art.

To eliminate the chlorinated by-product(s) from the fluorination system, further distillation of the high-boiling fraction stream 158 is usually required. As shown, the high-boiling fraction stream 158 is fed to a second distillation unit 105. Using conventional distillation techniques, the second distillation unit generates a low-boiling fraction stream 159 and a high-boiling fraction stream 160. Stream 160 contains the chlorinated by-products such as HCFC-132b, HCFC-122, and HCFC-112, which generally are considered undesirable and are removed from the system and disposed of.

The low-boiling fraction stream 159, which comprises fluorination agent and fluorinated intermediates, may be recycled back to the reactor 101 or condensed and used as a scrubbing liquid in the catalyst stripper 102.

Alternatively, low-boiling fraction stream 159 may be preferable to recover the fluorinated intermediate from stream 159 as a co-product of the fluorination. For example, in the manufacture of HFC-143a, it is desirable to recover HCFC-142b from the product stream. To this end, the low-boiling fraction stream 159 is fed to a phase separator 106. The phase separator 106 separates stream 159 to form a high-fluorination agent stream 162 and a low-fluorination stream 161. Before being returned to the reactor 101, stream 162, comprising a high concentration of fluorination agent, for example, HF, preferably is superheated in preconditioner (not shown) to add heat to the reaction. Stream 161 contains the fluorinated intermediate which is recovered using conventional purification techniques, typically distillation.

The examples described below are illustrative of the practice of the invention.

EXAMPLES

The first group of examples compares the operating conditions of conventional fluorination (Examples C-1 to C-3) to those of the present invention (Example 1). The test conditions and results are shown in Table 1 below.

In each test, liquid antimony pentachloride ($SbCl_5$) catalyst and liquid 1,1,1-trichloroethane (HCC-140a) were charged to the reactor to attain the desired catalyst concentration and reactor liquid level. Chlorine liquid was metered into the reactor to keep the catalyst in the pentavalent state. The reaction proceeded readily as gaseous hydrofluoric acid and liquid 1,1,1-trichloroethane were metered into the reactor. Steam was introduced into the reactor jacket to maintain reactor temperature as the reactor liquid began to cool from vaporization of low boiling product. Reaction product vapors entered the bottom of a 30 tray catalyst stripper distillation column equipped with a vertically mounted shell and tube heat exchanger which functions as a partial condenser. Crude product with HCl and HF exiting the partial condenser pressure control valve were scrubbed with water and caustic solution, dried, and compressed for distillation.

During batch flash distillation of by-products (after each operation in Examples C-1, C-2, & C-3) vapors exiting the catalyst stripper partial condenser were redirected to separate collection system to collect and quantify by-products.

In Example 1, by-products were separated and discharged to a collection vessel from the bottom of a distillation column downstream of scrubbing and compression. By-products have been analyzed and are mainly comprised of HCFCs-132b ($CF_2ClCFl_2Cl$), -121 ($CCl_2FCCl_2H$), and -122 ($CHCl_2FCCl_2F$); CFC-112 ($CCl_2FCCl_2F$); and HCCs-1130 (CHCl=CHCl), -1120 ($CCl_2$=CHCl), and -1110 ($CCl_2$=$CCl_2$).

TABLE 1

| Ex. Nos. | Temp (° F.) | Press (psig) | Total feed HCC140a (lbs) | Total by-product collected (lbs) | Ratio of by-product to HCC-140a | Period of Operation (days) | Comments and Observations |
|---|---|---|---|---|---|---|---|
| C-1 | 120 | 100 | 1,500,000 | 48,000 | 0.032 | 30 | Reactor liquid level increased; required frequent shutdown to boil off by-products from reactor. |
| C-2 | 90 | 60 | 593,000 | 25,000 | 0.043 | 19 | Reactor liquid level increased; required frequent shutdown to boil off by-products from reactor. |
| C-3 | 140 | 90 | 480,000 | 14,000 | 0.030 | 7 | Reactor liquid level increased; 7 day cycle- 5 day operation, 2 days to boil off by-products @ 250 F. |
| 1 | 200 | 50 | 4,500,000 | 94,000 | 0.021 | Continuous | Continuous operation. By-product collected from downstream distillation column bottoms. |

These examples show that operation at the temperature and pressures shown in Examples C-1, C-2, and C-3 retains high-boiling by-products in the reactor and requires shut-down of feeds and production in order to boil or remove the by-products from the reactor. By increasing the temperature and reducing the pressure according to the present invention, as shown in Example 1, the reactor is operated continuously without need to remove high-boiling by-products separately.

What is claimed is:

1. A process for producing a fluorinated organic compound comprising:

forming said fluorinated organic compound and one or more chlorinated organic by-products, which have a higher boiling temperature than the boiling temperature of said fluorinated organic compound, by reacting, in a reaction mixture, a liquid organic starting material with a fluorination agent in the presence of a liquid fluorination catalyst under conditions that effect the vaporization of one or more of said chlorinated organic by-products such that the accumulation of said chlorinated organic by-products in said reaction mixture is no greater than about 2% by weight of said starting material, and that produce a product stream containing said fluorinated organic compound in gaseous form and said one or more chlorinated organic by-products in gaseous form; and recovering said fluorinated organic compound from said product stream.

2. The process of claim 1, wherein said conditions include temperature and pressure conditions which are interrelated so as to produce said product stream.

3. The process of claim 2, wherein said pressure is maintained between about 50 and about 250 psig and said temperature is maintained between about 60 and about 120° C.

4. The process of claim 3, wherein said pressure is maintained between about 50 and about 100 psig and said temperature is maintained between about 70 and about 100° C.

5. The process of claim 1, wherein said fluorinated product is selected from the group consisting of HFC-143a, HFC-133a, HFC-236fa, HFC-245fa and one or more chlorinated by products includes one or more compounds selected from the group consisting of HCFC-132b, HCFC-123, HCFC-226, HCFC-235.

6. The process of claim 5, wherein said pressure and temperature are sufficient to substantially vaporize one or more compounds selected from the group consisting of HCFC-132b, HCFC-123, HCFC-226, HCFC-235.

7. The process of claim 6, wherein said fluorinated product is HFC-143a, and wherein said pressure and temperature are sufficient to vaporize HCFC-132b.

8. The process of claim 1, further comprising:

recovering said one or more chlorinated by-products from said product stream.

9. The process of claim 8, wherein recovering said fluorinated product from said product stream comprises:

distilling said product stream to produce a low-boiling fraction stream and a high-boiling fraction stream; and wherein the recovery of said one or more chlorinated by-products from said product stream comprises:

distilling said high-boiling fraction stream to produce a second low-boiling fraction stream and a second high-boiling fraction stream, said second high-boiling stream comprising chlorinated by-products.

10. The process of claim 9, further comprising:

recycling at least a portion of said second high-boiling fraction stream back to said reactor.

11. The process of claim 9, wherein said fluorinated organic is HFC-143a and said organic starting material is 1,1,1-trichloroethane, and wherein said method further comprising:

phase separating said second low-boiling fraction stream to form a high-fluorination agent content stream and a low-fluorination agent content stream;

recovering HCFC-142b from said low-fluorination agent content stream; and recycling said a high-fluorination agent content stream back to said reactor.

12. The process of claim 1, wherein said catalyst is present in an amount of about 5% to about 80% by weight of the reaction mixture.

13. The process of claim 12, wherein said catalyst is present in an amount of about 15% to about 50% by weight of the reaction mixture.

14. The process of claim 1, wherein said conditions are such that the accumulation of said chlorinated organic by-products in said reaction mix is no greater than about 1% by weight of said starting material.

15. The process of claim 14, wherein said conditions are such that the accumulation of said chlorinated organic by-products in said reaction mix is essentially zero.

16. The process of claim 1, wherein said conditions are such that no less than 50% by weight of the chlorinated organic by-products are vaporized.

17. The process of claim 16, wherein said conditions are such that no less than 75% by weight of the chlorinated organic by-products are vaporized.

18. The process of claim 17, wherein said conditions are such that essentially all of the chlorinated organic by-products are vaporized.

19. The process of claim 1, wherein said conditions are such that reaction pressure is about the minimum required to vaporize essentially all of the chlorinated by-products for a given temperature.

20. A process for producing a fluorinated organic compound comprising:

reacting a reaction mixture comprising at least an organic starting material and a fluorination agent in the presence of a liquid catalyst under conditions that are sufficient to vaporize by-products of said reaction such that the accumulation of said by-products in said reaction mixture is no greater than about 2% by weight of said organic starting material, and that produce a product stream containing said fluorinated organic compound and said by-products; and recovering said fluorinated organic compound from said product stream.

* * * * *